United States Patent [19]

Nishioka et al.

[11] Patent Number: 4,843,238
[45] Date of Patent: Jun. 27, 1989

[54] METHOD FOR IDENTIFYING A BLISTERED FILM IN LAYERED FILMS

[75] Inventors: Tadashi Nishioka; Hiroaki Morimoto Both of Italy; Yoji Mashiko; Hiroshi Koyama, both of Italy, all of Japan

[73] Assignee: Mitsubishi Denki Kabushiki Kaisha, Japan

[21] Appl. No.: 155,101

[22] Filed: Feb. 11, 1988

[30] Foreign Application Priority Data

Feb. 13, 1987 [JP] Japan ................................. 52-32003

[51] Int. Cl.⁴ ...................... G01D 18/00; G01N 23/00
[52] U.S. Cl. .................................. 250/252.1; 250/309; 250/492.3; 219/121.85
[58] Field of Search ........... 250/309, 492.21, 252.1 R, 250/397; 219/121.6, 121.85

[56] References Cited

U.S. PATENT DOCUMENTS

| | | | |
|---|---|---|---|
| 3,916,190 | 10/1975 | Valentine | 250/309 |
| 4,322,253 | 3/1982 | Pankoue | 219/121.6 |
| 4,503,329 | 3/1985 | Yamaguchi | 250/492.21 |
| 4,661,702 | 4/1987 | Welkie | 250/309 |
| 4,740,698 | 4/1988 | Tamura et al. | 250/309 |

OTHER PUBLICATIONS

Y. Tsaur et al., "Inert-Gas-Bubble Formation in the Implanted Metal/Si System" *Journal of Applied Physics* 50 (60), Jun. 1979, pp. 3978-3984.

H. Harada et al., "Trapped Ar Induced Deformation of Magnetron Sputter Al Film Overlaid with Plasma SiN Film", *Japanese Journal of Applied Physics*, vol. 21 (1982) Supplement 21-1, pp. 205-209.

Y. Mashiko et al., "Effects on Ion-Implantation-Induced Damages and Impurity on Platinum Silicide Formation", *Journal of Applied Physics* 53 (9), Sep. 1982, pp. 6144-6147.

*Primary Examiner*—Bruce C. Anderson
*Attorney, Agent, or Firm*—Leydig, Voit & Mayer

[57] ABSTRACT

In a method for identifying blistered film in layered films, a focused ion beam irradiates the approximate center of the blister and a portion which has no blister, and individual sets of the measurement data relating to the respective numbers of secondary electrons generated by the irradiation are compared to determine which film of layered films has blistered. Since the focused ion beam is employed, the present method is applicable to the detection of a small blister in layered films. Furthermore, since an enormous number of cutting operations as might have been required in the prior art are eliminated, the present method can be carried out, stably, positively and economically.

9 Claims, 5 Drawing Sheets

METHOD FOR IDENTIFYING A BLISTERED FILM IN LAYERED FILMS

BACKGROUND OF THE INVENTION

The present invention relates generally to a method for determining a blistered film in layered films and, more particularly, to a method for identifying which film of the layered films has blistered. For example, blisters may be formed in the layered films when a semiconductor wafer having a plurality of kinds of layered films is subjected to heat treatment during a process for producing a semiconductor device.

As the scale of integration in semiconductor devices increases and the structure thereof becomes more complicated, semiconductor devices are constituted by more and more kinds of films such as insulating films, conductive films, and metal films. In addition, the thickness of each film has been extremely reduced. In a typical process for producing semiconductor devices, many kinds of films are layered one on top of another in a predetermined sequence. At a predetermined stage of the production process, heat treatment is often effected on a semiconductor wafer having the layered films. In this case, as the result of heat treatment, a blister is often formed in the layered films because of differences in thermal expansion coefficients among the various films, or because of the discharge of gases contained therein. The presence of such a blister in a layered film not only makes it difficult to form a fine pattern, but also causes electrical defects or failures such as broken wires and short-circuits. In addition, this may produce adverse influences such as a reduction in the product yield of semiconductor devices or a reduction in the reliability thereof.

Accordingly, in a case where a blister is formed in layered films, determining which film of the layered films is blistered has become increasingly important in acquiring information relative to improvements in the structure, film material, production methods and so forth of semiconductor devices.

In a prior art method for identifying a blistered film in layered films, a semiconductor wafer is cut, and the cut cross section thereof is observed by means of an optical microscope or scanning type electron microscope, to thereby determine which film of the layered films has blistered.

However, the above-described prior art method for determining a blistered film involves the following disadvantages. In the prior art method, it is extremely difficult to cut a semiconductor wafer so as to slice a blister exactly in a crosswise direction thereof. In addition, since the size of a blister formed in a film on a semiconductor wafer is usually quite small, it is very rare for a single cutting operation to provide a sample including a blister which is cut exactly crosswise. Therefore, a desired sample cannot be obtained until a multiplicity of cutting operations are repeated and hence a significant number of semiconductor wafers are wasted. Accordingly, such a method for determining a blistered film by cutting a semiconductor wafer is unstable, unreliable, complicated and uneconomical.

SUMMARY OF THE INVENTION

Accordingly, an object of the present invention is to eliminate the above-described disadvantages of the prior art.

Another object of the present invention is to provide a method for determining which film of layered films has blistered by irradiating a focused ion beam on a portion having no blister and on the approximate center of a blister and comparing data measuring the number of secondary electrons generated by such irradiation.

In order to achieve the above object, according to an aspect of the present invention, there is provided a method for identifying a blistered film in layered films, comprising: a first step of irradiating a focused ion beam onto a portion which has no blisters in layered films having a blister, while measuring the number of secondary electrons generated by the irradiation as a function of time thereby providing a first set of measurement data corresponding to the number of secondary electrons; a second step of irradiating the focused ion beam onto the approximate center of the blister in the layered films while measuring the number of secondary electrons generated by the irradiation as a function of time thereby providing a second set of measurement data corresponding to the number of secondary electrons; and a third step of comparing the first set of measurement data obtained in the first step with the second set of measurement data obtained in the second step so as to determine the kind of film having the blister.

In accordance with the present invention, when the focused ion beam having a reduced beam diameter and including ions at a high density is irradiated on the surface of the layered films, constituent atoms of the uppermost film of the layered films on which portion the focused ion beam is irradiated receive the energy of the focused ion beam and scatter, the so-called sputtering phenomenon occuring thereby excavating the irradiated portion of the film. At the same time, secondary electrons are generated from the constituent elements of the film irradiated with the focused ion beam. If there is no barrier which prevents the secondary electrons from flying, almost all of them are collected by a secondary electron collector which is disposed in the vicinity of the portion irradiated with the focused ion beam and in a spaced relationship with the uppermost surface of the layered films. If there is some barrier preventing the flying of the secondary electrons in the flight path, the number of secondary electrons collected by the secondary electron collector becomes smaller than the number of secondary electrons which are generated from the film by the irradiation of the focused ion beam. This phenomenon is encountered when the focused ion beam irradiates the approximate center of a blister. More specifically, the approximate center of the blister is irradiated with the focused ion beam until the blistered portion of the film is excavated. After completion of this excavation, the excavation of the next film which has no blister is initiated. The geometrical situations and the distribution of an electric field which surround the secondary electrons generated from the non-blistered film during the excavation are different from those which surround an irradiated portion having no blister. This difference is partly due to the presence of a void formed between the blistered film and the nonblistered film. If such a void is present, the secondary electrons generated from the nonblistered film are partly trapped within the void. Accordingly, the number of secondary electrons which are thus collected and captured by the secondary electron collector (hereinafter referred to simply as "collected secondary electrons") becomes smaller than the number of secondary electrons generated from the nonblistered film by the irradiation of the focused ion beam. More specifically, even if the intensity of the beams and the level of energy in the focused ion beam are fixed, the number of collected secondary electrons captured by the second electron collector varies as the excavation proceeds. Of course, variations in the number of collected secondary electrons include variations derived from a difference between the generation rate of secondary electrons in different kinds of films of the layered films.

In the method of the present invention, the number of collected secondary electrons which varies as the excavation proceeds, that is, which varies over the irradiation time of the focused ion beam is obtained as measured data as a function of time. The acquisition of data is effected with respect to the approximate center of a blister and a portion which has no blister.

By the comparison of the measured data relative to the number of collected secondary electrons generated from the approximate center of the blister with that of collected secondary electrons generated from the portion which has no blister, it is possible to determine what film of the layered films has blistered. Namely, while the focused ion beam is irradiating and excavating the blistered films, no discrepancy occurs between the respective sets of measurement data. However, when the non-blistered film below the blistered films starts to be excavated by the irradiation, a discrepancy appears between respective sets of measurement data. In particular, the point of time at which the number of collected secondary electrons rapidly decreases which is contained in the measurement data of the number of collected secondary electrons generated from the approximate center of the blister in the layered films provides information which is very useful in determining the kind of blistered film. Accordingly, it is found that the step of the excavation process which corresponds to the time at which the discrepancy clearly appears represents the boundary between the blistered film and the nonblistered film. It is noted that variations derived from a difference between the generation rates of secondary electrons from different kinds of films does not influence the result of the determination because there is no discrepancy in the measurement data relative to these blistered films while the focused ion beam is irradiating and excavating the blistered films.

It is evident from the foregoing that the method for identifying a blistered film in layered films in accordance with the present invention differs from the prior art method in which a semiconductor wafer substrate is cut. In the present invention, the focused ion beam is irradiated on both the approximate center of a blister and on a portion which has no blister. Accordingly, it is utterly unnecessary to perform the operation of cutting the blister crosswise. In addition, since a focused ion beam is employed, the present invention is applicable to the detection of small blisters in layered films. Furthermore, since the enormous number of cutting operations that are sometime required in the prior art is eliminated, the present invention can be carried out stably, reliably and economically.

BRIEF DESCRIPTION OF THE DRAWINGS

The present invention will be more readily apparent from the following detailed description of a few preferred embodiments thereof when taken in conjunction with the accompanying drawings, in which:

FIGS. 1a to 1f are graphs showing measurement data which corresponds to the respective process steps as shown in FIGS. 1A to 1F;

FIGS. 2a to 2f are graphs showing measurement data which correspond to the respective process steps as shown in FIGS. 2A to 2F.

DESCRIPTION OF THE PREFERRED EMBODIMENTS

FIGS. 1A to 1F and FIGS. 1a to 1g illustrate a first preferred embodiment of the present invention. In these figures, the same reference numerals are used to denote the same or corresponding portions.

Figures 1A, 1B, 1C:
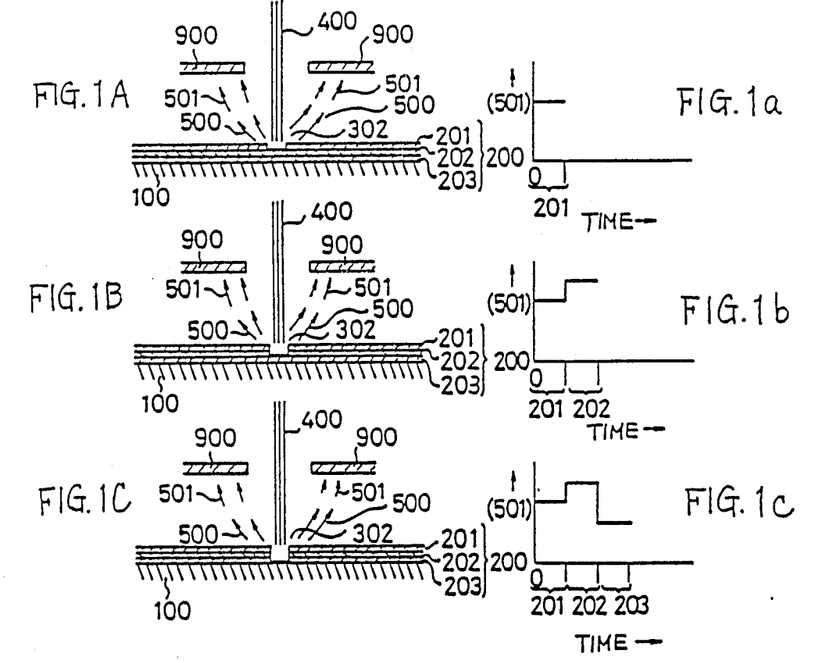
FIGS. 1A to 1F are diagrammatic cross sectional views of a semiconductor device illustrating the principle of a method for identifying a blistered film in layered films in accordance with the present invention.
Figure 1D:
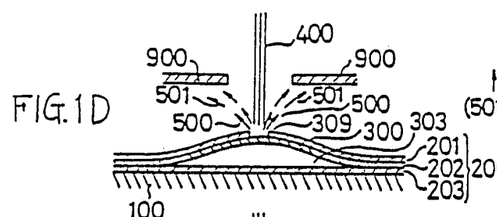

In FIGS. 1A to 1F, a substrate 100 of a semiconductor wafer is formed of, for example, Si or GaAs, and layered films 200 are formed on the substrate 100. The layered films 200 include a plurality of films 201, 202 and 203 which are respectively constituted by different kinds of material such as $SiO_2$, SiN or polycrystalline silicon. As shown in FIG. 1D, a blister 300 is formed in the layered films 200, and a void 303 is formed between the film 202 and the film 203. A focused ion beam 400 having a reduced cross section and including ions such as $Ga^+$ or $Si^+$ at a high density is irradiated on the layered films 200. In FIGS. 1A to 1C, the focused ion beam 400 is irradiated on a portion 302 where there is no blister 300, whereas in FIGS. 1D to 1F, the focused ion beam 400 is irradiated on the approximate center 301 of the blister 300. The irradiation of the focused ion beam 400 causes the generation of secondary electrons 500 from the layered films 200, and the thus-generated secondary electrons 500 are collected by secondary electron collectors 900 which are disposed in the vicinity of positions irradiated by the focused ion beam 400.

It is noted that an active or passive element may be embedded in the substrate 100. Although not specifically shown, the substrate 100 is carried by a table which is movable in two dimensions. Therefore, the focused ion beam 400 is also functional for irradiating the substrate 100 with two dimensional movement or scanning. The two-dimensional movement or scanning of the focused ion beam 400 operates under computerized control. The secondary electron collector 900 has an opening which allows the secondary electrons 500 to be collected as collected secondary electrons 501, without preventing the focused ion beam 400 from irradiation while moving or scanning in two dimensions.

At first, as shown in FIG. 1A, the focused ion beam 400 is irradiated on the portion 302 which has no blister 300. The thus irradiated portion of the film 201 is excavated by sputtering, and, at the same time, the secondary electrons 500 are generated from the film 201. The thus generated secondary electrons 500 are guided toward the second electron collector 900 by an electric field formed between the substrate 100 and the secondary electron collector 900. In this case, since there is no barrier between the film 201 and the secondary electron collector 900, almost all of the secondary electrons 500 are collected by the secondary electron collector 900. The number of collected secondary electrons 501 collected by the secondary electron collector 900 while the focused ion beam 400 is irradiating the film 201, is measured as a function of time and stored in the form of time series data which corresponds to the irradiation time. This time series data of the number of collected secondary electrons 501 is shown in FIG. 1a. FIGS. 1b to 1f are also graphs corresponding to FIGS. 1B to 1F, respectively, and each illustrate time series data representative of the number of collected secondary electrons 501 which is measured during the steps shown in each of FIGS. 1B to 1F.

The irradiation of the focused ion beam 400 proceeds until the irradiated portion of the film 201 has been completely excavated. Subsequently, the corresponding portion of the film 202 is excavated by the focused ion beam 400 as shown in FIGS. 1B and 1b. After the completion of the excavation of the irradiated portion of the film 202, the film 203 is likewise excavated as shown in FIGS. 1C and 1c. In this manner, the focused ion beam 400 irradiates and excavates the portion 302 through the whole layer of films 200 which has no blister 300. At this stage, the irradiation of the focused ion beam 400 is temporarily halted.

Then, as shown in FIG. 1D, the focused ion beam 400 irradiates the approximate center 301 of the blister 300 by moving the substrate 100, deflecting the focused ion beam 400, or a combination of both. When the focused ion beam 400 irradiates the approximate center 301 of the blister 300, the time series data of the number of collected secondary electrons 501 while each of the films 201 and 202 is being excavated by the irradiation is similar to the time series data obtained while each of the films 201 and 202 of the portion 302 which has no blister was excavated by the irradiation. This similarity in time series data is due to the following reason. While each of the films 201 and 202 are being excavated by the irradiation, the secondary electrons 500 are capable of flying toward the secondary electron collector 900 without striking any barrier. Accordingly, almost all of the secondary electrons 500 are collected by the secondary electron collector 900 in the form of the collected secondary electrons 501.

However, when the focused ion beam 400 starts to excavate the film 203 after the beam 400 has excavated the films 201 and 202, the circumstances change. Namely, as shown in FIGS. 1F, the focused ion beam 400 passes through the excavated portions of the films 201 and 202, and further through the void 303 which forms the blister 300, to irradiate the film 203, thereby generating the secondary electrons 500. As illustrated in FIG. 1F, the portion from which the secondary electrons 500 are generated is substantially covered by the films 201 and 202. Therefore, the strength of the electric field of the secondary electron collector 900 which acts to attract the secondary electrons 500 is reduced. In addition, the solid angle through the portion from which the secondary electrons 500 are generated facing the opening formed in the films 201 and 202 is small. Accordingly, when the portion of the film 203 over which the void 303 is formed is irradiated with the focused ion beam 400, only a few of the secondary electrons 500 are collected as the collected secondary electrons 501. As can be seen from FIG. 1f which illustrates this situation, the number of secondary electrons 501 which are collected while the film 203 is being excavated is extremely small.

Figure 1E:
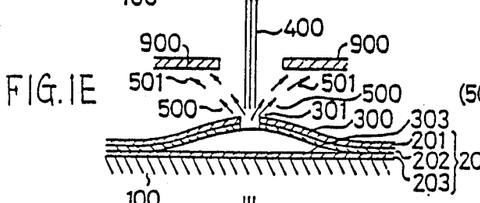
Figure 1F:
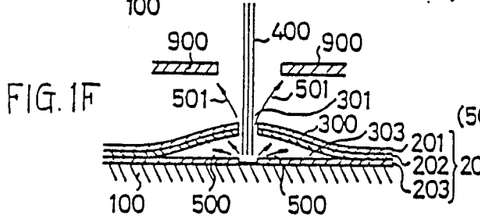

Hereinafter, the treatments shown in FIGS. 1A to 1C are referred to simply as a "first step", and the treatments shown in FIGS. 1D to 1F are referred to simply as a "second step". A set of time series data representative of the number of collected secondary electrons 501 obtained in the first step is compared with a set of time series data representative of the number of collected secondary electrons 501 obtained in the second step. In consequence, as described previously, it can be determined that a blister 300 is formed in the film 202. This comparison between sets of time series data representative of the numbers of collected secondary electrons 501 is hereinafter referred to as a "third step".

Figure 1G:
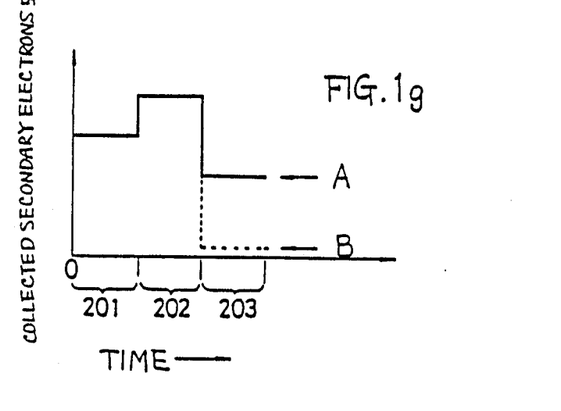
FIG. 1g is a graph showing measurement data relating to the numbers of secondary electrons collected from the approximate center of a blister and from a portion which has no blister as shown in FIGS. 1a to 1f.

As shown in FIG. 1g, while the films 201 and 202 are being irradiated with the focused ion beam 400, the number of collected secondary electrons 501 varies in the same manner and at the same timing, irrespective of whether the focused ion beam 400 irradiates the portion 302 which has no blister 300 or the approximate center 301 of the blister 300. However, while the film 203 is being irradiated with the focused ion beam 400, the numbers of collected secondary electrons 501 clearly differ from each other, as indicated by arrows A and B in FIG. 1g, depending upon whether the focused ion beam 400 irradiates the portion 302 which has no blister or the approximate center 301 of the blister 300. Accordingly, in the third step, the kind of film which has formed a blister in the layered films can be determined exactly and easily.

As one example of the above-described embodiment, a focused ion beam 400 was used in which the kind of ions were Ga+, the level of energy was 30 KeV, the beam diameter was 0.3 $\mu$m, and the ion density was $10^{17}$ ions cm$^2$, and the construction of layered films used was Al/SiN/Al/SiO$_2$/Si. This, focused ion beam 400 was applied to blisters which were formed between the Al/SiN and Al/SiO$_2$/Si films by voids having a diameter of 30 to 50 $\mu$m and a thickness of 1.0 to 2.5 $\mu$m. In consequence, it was found possible to determine that the kind of film which formed the blister was SiN.

FIGS. 2A to 2F are diagrammatic cross sections of a semiconductor device which illustrate a process sequence for effecting another embodiment of the present invention. FIGS. 2a to 2f are graphs corresponding to FIGS. 2A to 2F, respectively.

In this embodiment, the first and second steps which were explained in the embodiment described previously in conjunction with FIGS. 1A to 1g are partially effected by using the focused ion beam 400 of a predetermined irradiation time, and then the third step is partially performed. Subsequently, these steps are repeated in this sequence in rotation until the entire process is completed.

First of all, the coordinates of the respective positions of the approximate center 301 of the blister 300 and the portion 302 which has no blister are previously stored in, for example, a computer (not shown) which controls the two-dimensional movement and scanning of the substrate 100 and the focused ion beam 400.

Figure 2A:
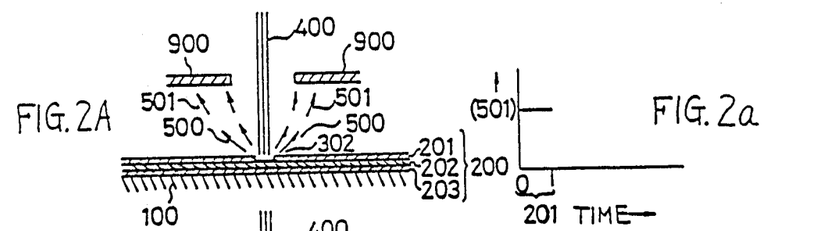
FIGS. 2A to 2F are cross sections of a semiconductor device according to one preferred embodiment of the present invention.

Secondly, as shown in FIG. 2A, the substrate 100 is moved or the focused ion beam 400 is deflected so that the focused ion beam 400 irradiates the portion 302 which has no blister 300, and the coordinates of that position are stored. Then, the portion 302 which has no blister 300 is irradiated with the focused ion beam 400 over a predetermined irradiation time. The number of secondary electrons 501 collected during this irradiation are measured and stored in the form of time series data.

Figures 2B, 2C:
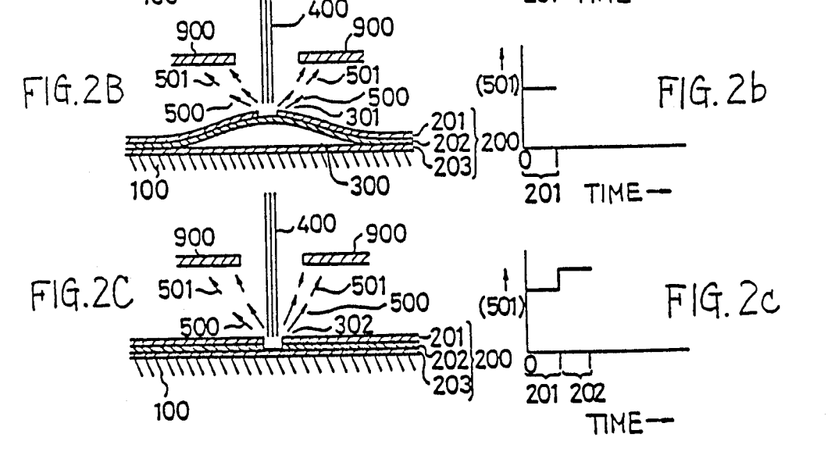
Figure 2D:
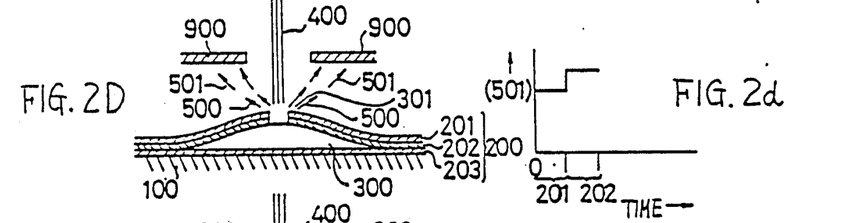
Figures 2E, 2F:
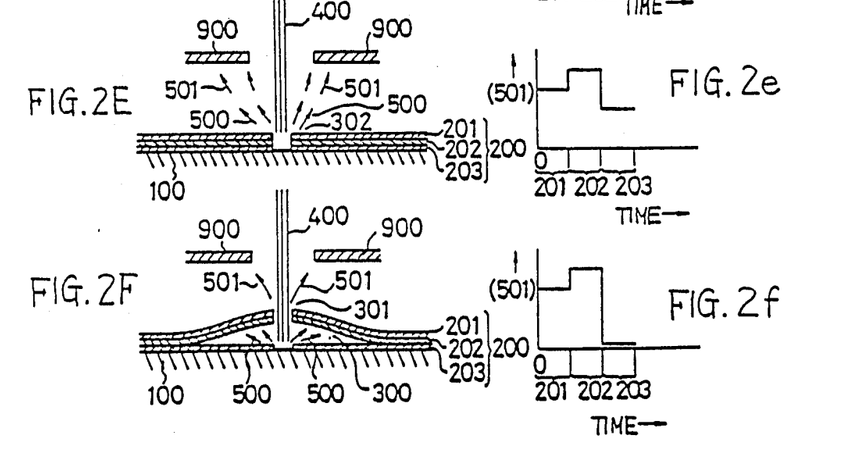

Thirdly, as shown in FIG. 2B, the substrate 100 is moved or the focused ion beam 400 is deflected so that the focused ion beam 400 irradiates the approximate center 301 of the blister 300, whose coordinates have been stored. Then, the approximate center 301 of the blister 300 is irradiated with the focused ion beam 400 for the predetermined irradiation time. The number of secondary electrons 501 collected during this irradiation is measured and stored in the form of time series data. Subsequently, the number of collected secondary electrons 501 from the portion 302 which has no blister is compared with that of the collected secondary electrons 501 from the approximate center 301 of the blister 300.

One cycle consisting of the first step of irradiating the portion 302 which has no blister, the second step of irradiating the approximate center 301 of the blister 300, and the third step of comparing the numbers of collected secondary electrons 501 is repeated on each of the films 201, 202, and 203 by the irradiation with the focused ion beam 400 over the predetermined period, as sequentially shown in FIGS. 2C, 2D, 2E and 2F. In the third step in which the numbers of collected secondary electrons 501 are mutually compared, if a predetermined disparity appears, the irradiation with the focused ion beam 400 is halted and it is determined that the film 202 has formed the blister 300.

In FIGS. 2A to 2F and 2a to 2f, the irradiation time in each of the first and second steps and the frequency of repetitions thereof are shown as being equal to the irradiation time for excavating the films 201, 202 and 203 and the frequency of repetitions. However, the irradiation time in each of the first and second steps may be shortened and, instead, the frequency of repetitions of the first, second, and third steps may be increased. In consequence, the discrepancy between the numbers of collected secondary electrons 501 in the first and second steps can be detected and compared in detail in the depthwise direction of the layered films 200. In addition, immediately after the film which has formed the blister 300, in this example the film 202, has been detected and determined, the irradiation with the focused ion beam 400 can be stopped, whereby it is possible to prevent unnecessary excavation of the substrate 100 or the layered films 200.

Figure 3A:
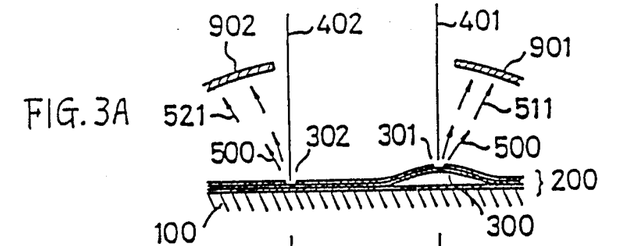
FIGS. 3A to 3C are diagrammatic cross sections of a semiconductor device according to another preferred embodiment of the present invention.
Figure 3B:
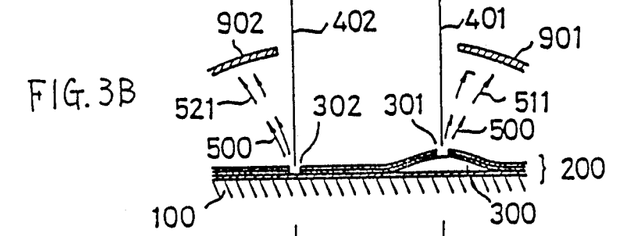
Figure 3C:
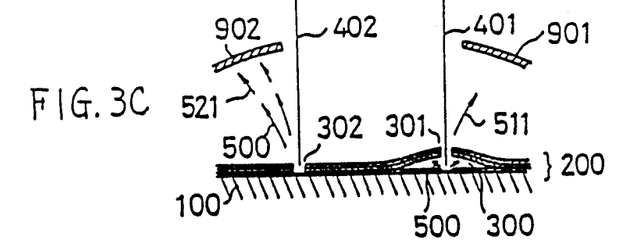

FIGS. 3A to 3C are diagrammatic cross sections of a semiconductor device, and illustrate a process sequence for effecting still another embodiment of the present invention. As illustrated, a focused ion beam 401 irradiates only the approximate center 301 of the blister 300, while a focused ion beam 402 irradiates only the portion 302 which has no blister. Ion beam sources (not shown) for generating the focused ion beams 401 and 402 are disposed independently of each other. In addition, a first secondary electron collector 901 is so disposed as to collect secondary electrons 500 scattered from the approximate center 301 of the blister 300, while a second secondary electron collector 902 is so disposed as to collect secondary electrons 500 scattered from the portion 302 which has no blister 300. The first secondary electron collector 901 collects the secondary electrons 500 in the form of collected secondary electrons 511. The second secondary electron collector 902 collects the secondary electrons 500 in the form of collected secondary electrons 521. The first secondary electron collectors 901 and the second secondary electron collector 902 are disposed independently of each other. The relationship between the positions of the collectors 901 and 902 is selected so that the secondary electrons 500 from the portion 302 and the blister 300 may be separately collected as the collected secondary electrons 511 and 521, and so as not to prevent the irradiation with the focused ion beams 401 and 402.

In the above-described embodiment, the first step and the second step which have been described in conjunction with FIGS. 1A to 1g are effected at the same time by the irradiation with the two independently focused ion beams 401 and 402 over a predetermined irradiation time. Subsequently, the third step is performed. These steps are repeated to complete the entire process.

More specifically, in this embodiment, the focused ion beams 402 and 401 are respectively made to irradiate the portion which has no blister and the approximate center 301 of the blister 300 at the same time as shown in FIG. 3A. The secondary electrons 500 scattered by the focused ion beams 401 and 402 are collected by the first and second secondary electron collectors 901 and 902, respectively, in the form of the collected secondary electrons 511 and 512. The thus-obtained sets of measurement data are immediately compared with each other. A similar operation is repeated with the focused ion beams 401 and 402 over a predetermined irradiation time in accordance with the process sequence as shown in FIGS. 3B and 3C. If a predetermined discrepancy appears in a comparison between the respective sets of measurement data of the collected secondary electrons 511 and 521, the irradiation with the focused ion beams 401 and 402 is stopped to determine the kind of film which forms the blister 300, in this example the film 202.

In accordance with the above-described embodiment, it is possible to simultaneously obtain the measurement data representative of the numbers of collected secondary electrons 511 and 521 which are respectively obtained in the first and second steps. Accordingly, the resultant discrepancy can be examined in a short time to detect and determine the film 202 which forms the blister 300. Also, if the irradiation time of the focused ion beams 401 and 402 is shortened and the frequency of repetitions of the steps is increased, the film 202 which forms the blister 300 can be detected and compared in detail in the depthwise direction of the layered films 200. After the film 202 which forms the blister 300 has been detected and identified, the irradiation with the focused ion beams 401 and 402 can be immediately halted, whereby it is possible to prevent unnecessary excavating of the substrate 100 or the layered films 200.

In the respective above-described embodiments, prior to the performance of each of the embodiments, a film other than the films 201, 202 and 203 which constitute the layered films 200, for example, an electrically conductive film, may be formed over the layered films 200 to cover at least the approximate center 301 of the blister 300 and the portion 302 which has no blister, the portions 301 and 302 being irradiated with at least one of the focused ion beams 400, 401 and 402. Subsequently, the present invention may be applied to the thus-produced semiconductor device. Accordingly, even if another kind of film or layered films are formed on the layered films 200, the effect and function of the present invention can be achieved since the numbers of collected secondary electrons 501, 511 and 521 are compared to detect any discrepancy therebetween. In a case where the layered films 200 are constituted by, for example, an electrically insulating film, if an electrically conductive film, for example, a metal film is formed over the uppermost film 201 of the electrically insulating film, it is possible to prevent charging up of the electrically insulating films 201 and 202 such as is often caused by irradiation with focused ion beams 400, 401 and 402. Accordingly, the numbers of collected secondary electrons 501, 511 and 521 can be measured precisely with good reproducibility, whereby it is possible to exactly determine the film 202 which forms the blister 300.

While a few presently preferred embodiments of the present invention have been shown and described herein, it will be apparent to those skilled in the art that various changes and/or modifications thereof can be made without departing from the spirit and scope of the invention as define in the appended claims.

What is claimed is:

1. A method for identifying a blistered film in layered films comprising:
    a first step of irradiating with a focused ion beam a portion, which has no blister, of layered films having a blister while measuring the number of secondary electrons generated by said irradiation as a function of time, thereby providing a first set of measurement data corresponding to said number of the second electrons;
    a second step of irradiating with said focused ion beam the approximate center of said blister in said layered films while measuring the number of secondary electrons generated by said irradiation as a function of time, thereby providing a second set of measurement data corresponding to said number of the secondary electrons; and
    a third step of comparing said first set of measurement data obtained in said first step with said second set of measurement data obtained in said second step to determine the kind of film having said blister.

2. A method for identifying a blistered film in layered films as claimed in claim 1 wherein said second set of measurement data obtained in said second step includes a point of time at which said number of secondary electrons rapidly decreases, said point of time being used as a reference point for determining in said third step said kind of film having said blister.

3. A method for identifying a blistered film in layered films as claimed in claim 1 wherein said blister and said non-blistered portion of said layered films which is irradiated with said focused ion beam are coated with a film which is different in kind from said layered films.

4. A method for identifying a blistered film in layered films as claimed in claim 3 wherein said film coated on said blister and said non-blistered portion of said layered films is an electrically conductive film.

5. A method for identifying a blistered film in layered films as claimed in claim 4 wherein said electrically conductive film is a metal film.

6. A method for identifying a blistered film in layered films as claimed in claim 1 wherein said first, second and third steps are sequentially carried out in that order.

7. A method for identifying a blistered film in layered films as claimed in claim 1 wherein said first and second steps are sequentially carried out for a predetermined period of time, respectively, and then said third step is carried out, these steps being thereafter repeated until said blistered film is identified.

8. A method for identifying a blistered film in layered films as claimed in claim 1 wherein said first and second steps are simultaneously carried out, then said third step is carried out, and thereafter said first and second steps and said third step are repeated sequentially in rotation.

9. A method for identifying a blistered film in layered film as claimed in claim 8 wherein said respective focused ion beams in said first and second steps irradiate said layered films independently of each other.

* * * * *